(12) United States Patent
Rochon

(10) Patent No.: US 6,346,279 B1
(45) Date of Patent: Feb. 12, 2002

(54) HYDROGEN PEROXIDE DISINFECTANT WITH INCREASED ACTIVITY

(75) Inventor: Michael J. Rochon, Caledon (CA)

(73) Assignee: Virox Technologies, Inc., Mississauga (CA)

(*) Notice: Subject to any disclaimer, the term of this patent is extended or adjusted under 35 U.S.C. 154(b) by 0 days.

(21) Appl. No.: 09/356,345

(22) Filed: Jul. 19, 1999

Related U.S. Application Data

(60) Provisional application No. 60/112,047, filed on Dec. 14, 1998.

(51) Int. Cl.[7] .............. A01N 59/00; A01N 59/26; A01N 41/04; A01N 25/22; A61L 2/18

(52) U.S. Cl. .............. 424/616; 424/601; 424/602; 424/603; 424/604; 424/605; 424/606; 424/126; 424/DIG. 6; 422/12; 422/28; 514/553; 514/557; 514/558; 514/559; 514/560; 514/574; 514/576; 514/709; 514/970; 504/151

(58) Field of Search .............. 424/616, 601–606, 424/126, DIG. 6; 514/557, 558, 559, 560, 574, 553, 576, 709, 970; 422/12, 28; 504/151

(56) References Cited

U.S. PATENT DOCUMENTS

| | | | |
|---|---|---|---|
| 4,051,058 A | * 9/1977 | Bowing et al. | 424/616 |
| 4,477,438 A | 10/1984 | Willcockson et al. | |
| 4,518,585 A | 5/1985 | Greene et al. | |
| 5,059,417 A | 10/1991 | Williams et al. | 424/616 |
| 5,171,564 A | 12/1992 | Nathoo et al. | 424/613 |
| 5,200,189 A | 4/1993 | Oakes et al. | 424/405 |
| 5,264,229 A | 11/1993 | Mannig et al. | |
| 5,523,012 A | 6/1996 | Winterton et al. | 424/78.04 |
| 5,641,530 A | 6/1997 | Chen | |
| 5,723,406 A | 3/1998 | Larose et al. | 504/114 |

FOREIGN PATENT DOCUMENTS

| | | |
|---|---|---|
| EP | 0087049 B1 | 11/1986 |
| EP | 0289463 A1 | 11/1988 |
| EP | 351772 | * 1/1990 |
| EP | 0845526 A2 | 6/1998 |
| GB | 2 101 350 A | 1/1983 |
| JP | 9-87677 | * 3/1997 |
| JP | 10-121097 | * 5/1998 |
| WO | WO93/14183 | 7/1993 |
| WO | WO98/11777 | 3/1998 |
| WO | 98/21305 | 5/1998 |

OTHER PUBLICATIONS

Sattar, Syed A. et al., "A product based on accelerated and stabilized hydrogen peroxide . . . " The Canadian Journal of Infection Control, Winter 1998, pp. 123–130.*

Chemical Abstracts 128:309723, abstracting JP 10–121097 (1998).*

JPAB Abstract, Pub–No. JP409087677A, abstracting JP 09087677 (1997).*

Chemical Abstracts 129:42635, abstracting JP 10–130693 (1998).*

Disinfection, Sterilization, and Preservation, 4th ed. Seymour S. Block, Lea & Febiger 1991 pp. 167–172, 178–180, 256–261, 263–271.

* cited by examiner

*Primary Examiner*—John Pak
(74) *Attorney, Agent, or Firm*—Ridout & Maybee, LLP

(57) ABSTRACT

An acidic aqueous hydrogen peroxid solution is provided, with improved disinfectant activity. Concentrated solutions preferably contain up to about 8% and as-used concentrations contain about 0.5% peroxide. The solution also contains from 0.1 to 5.0% of at least one acid compound, e.g. phosphoric and/or a phosphonate with from 1 to 5 phosphonic acid groups, and from 0.02 to 5% of at least one anionic surfactant. The surfactant is selected from C8 to C16-alkyl aryl sulphonic acids, sulphonated C12 to C22 carboxylic acids, C8 to C22-alkyl diphenyl oxide sulphonic acids, naphthalene sulphonic acids, C8 to C22 alkyl sulphonic acids, and alkali metal and ammonium salts thereof, and alkali metal C8 to C18 alkyl sulphates, and mixtures thereof. Most preferably the solution has an emulsifier, e.g. a salt of an alkylated diphenyl oxide. The solution may also contain corrosion inhibitors and/or lower alcohols.

14 Claims, No Drawings

HYDROGEN PEROXIDE DISINFECTANT WITH INCREASED ACTIVITY

This application claims the benefit of U.S. provisional patent application No. 60/112,047 filed Dec. 14, 1998.

FIELD OF THE INVENTION

The present invention relates to disinfectants, and in particular it relates to hydrogen peroxide solutions with improved disinfectant and antimicrobial properties.

BACKGROUND TO THE INVENTION

A wide range of disinfectants is known, as discussed for example in Disinfection, Sterilization, and Preservation, edited and partially written by Professor Seymour S. Block, Fourth Edition, published 1991 by Lea & Febiger, Pennsylvania. Certain peroxygen compounds, chlorine compounds, phenolics, quaternary ammonium compounds and surface active agents are known for their germicidal properties. The rate of disinfection is relatively slow in many cases, and some compounds emit volatile organic compounds or leave a persistent residue in the environment.

Hydrogen peroxide is finding favour in many applications because of the innocuous breakdown products of water and oxygen, and that it tends to have broad spectrum antimicrobial activity. Broad spectrum activity is important in situations where harmful organisms are present but their identity is not known. As hydrogen peroxide tends to be unstable and decomposes over time, steps must be taken to stabilize the hydrogen peroxide solutions if they are to be stored for any length of time. Various ways have been proposed to improve the stability of hydrogen peroxide compositions. For example, sodium stannate, sodium nitrate, and diethylene triamine penta(methylenephosphonic acid) have been reported as being useful as stabilizers, as disclosed in U.S. Pat. No. 5,523,012 to Winterton et al., which issued Jun. 4, 1996. Additionally, a major drawback of most disinfectants used heretofore has been the length of time needed to reduce the bacterial count after the disinfectant has been applied to a bacterially contaminated material. For example, it may take 30 minutes or more after application of the disinfectant to disinfect a treated surface. In many circumstances this rate of disinfection is far from satisfactory.

Combinations of hydrogen peroxide with various surfactants are known. For example, Winterton et al. discloses, in U.S. Pat. No. 5,523,012, a buffered disinfecting solution for contact lenses, which has from about 0.1% to about 1.0% of an ocularly compatible surfactant. Winterton disclosed that in one experiment, addition of about 0.4% anionic sulphosuccinate surfactant improved the killing time for *aspergillus fumigatus* to 6.9 minutes, compared to 9.4 minutes for a solution containing 0.1% nonionic surfactants. However, even 6.9 minutes is far too long for many applications.

The present invention is directed to improving the efficacy of hydrogen peroxide based solutions.

SUMMARY OF THE INVENTION

Accordingly the present invention provides an aqueous solution comprising i) hydrogen peroxide in a concentration of up to about 20 wt./wt. % of the solution, ii) at least one phosphorus-based acid in a concentration range of from 0.05 to 8.0 wt./wt. % of the solution, and iii) at least one anionic surfactant selected from the group consisting of C8 to C16-alkyl aryl sulphonic acids and alkali metal and ammonium salts thereof, sulphonated C12 to C22 carboxylic acids and alkali metal and ammonium salts thereof, C8 to C22-alkyl diphenyl oxide sulphonic acids and alkali metal and ammonium salts thereof, naphthalene sulphonic acids and alkali metal and ammonium salts thereof, C8 to C22 alkyl sulphonic acids and alkali metal and ammonium salts thereof, alkali metal C8 to C18 alkyl sulphates, and mixtures thereof, in a concentration range of from 0.02 to 5 wt./wt.% of the solution.

The pH of the solutions are preferably from about 1 to about 9, particularly from 1 to 7, and even more particularly from about 1 to about 3.

In one embodiment, the phosphorus-based acid is selected from the group consisting of phosphoric acid, phosphonates having from 1 to 5 phosphonic acid groups, and mixtures thereof.

In one embodiment, the phosphorus-based acid is selected from the group consisting of phosphoric acid, amino tri (methylene phosphonic acid), 1-hydroxyethylidene-1,1,-diphosphonic acid, diethylenetriaminepenta(methylene phosphonic acid), 2-hydroxyethylimino bis(methylene phosphonic acid), ethylene diamine tetra(methylene phosphonic acid) and mixtures thereof.

In a further embodiment, the solution contains up to about 3 wt./wt. % of at least one emulsifier.

In another embodiment, the emulsifier is selected from the group consisting of polyoxyethylene surfactants and hydrotropes, e.g. C8 to C16 alkylphenol alkoxylates. The hydrotrope may be selected from an alkylated sulphonated diphenyl oxide and an alkylated sulphonated diphenyl oxide sale. The emulsifier may be a C8 to C16 alkyl phenoxy-polyethoxy ethanol.

In yet another embodiment, the emulsifier is octylphenyl ethoxylate.

In another embodiment, the solution has a hydrogen peroxide concentration of from 0.05 to 8.0 wt./wt. % of the solution.

In yet another embodiment, the solution has a hydrogen peroxide concentration of from 0.05 to 1.0 wt./wt. % of the solution.

In a further embodiment, the hydrogen peroxide concentration is from 3.0 to 8.0 wt./wt. % of the solution.

In yet another embodiment, the alkyl aryl sulphonate is dodecyl benzene sulphonate or an alkali metal salt thereof or an ammonium salt thereof.

In another embodiment, the solution contains phosphoric acid, a phosphonate having from 1 to 5 phosphonic acid groups, an anionic alkyl aryl sulphonic acid, an alkylphenol alkoxylate and an alkylated sulphonated diphenyl oxide salt.

In another embodiment, the solution contains a corrosion inhibitor.

In a further embodiment, the corrosion inhibitor is selected from the group consisting of a benzotriazole, a hydrobenzotriazole, a carboxybenzotriazole, sodium nitrite, sodium molybdate, sodium gluconate and sodium benzoate and combinations thereof.

In yet another embodiment, the corrosion inhibitor is present in a concentration of from 0.05 to 10.0 wt./wt. % of the solution.

In another embodiment, the solution contains from 0.1 to 10.0 wt./wt % of a C1 to C6 alcohol, e.g. methanol, ethanol and isopropanol.

In another embodiment, the solution contains a mono-or poly-carboxylic acid or mixtures thereof, e.g. acetic acid, glycolic acid, citric acid, succinic acid, or mixtures thereof, in a concentration of from about 0.05 to about 4.0 wt./wt. %.

In a further embodiment, the solution contains a non-ionic surfactant selected from the group consisting of alkylated alkoxylate surfactants, alkyl aryl alkoxylate surfactants and mixtures thereof.

DETAILED DESCRIPTION OF PREFERRED EMBODIMENTS

In the past few years, efforts have been concentrated on developing chemicals that will be highly effective against microorganisms when highly diluted, will be low in toxicity to humans and other animals, and will not injure the environment. Of all the known disinfectants and antimicrobials, hydrogen peroxide appears to have exceptional potential, especially in terms of toxicity and injury to the environment because the decomposition products are benign. For example, at concentrations of 1–3 wt./wt. % aqueous solution, hydrogen peroxide is considered non-corrosive and non-irritating; at concentrations of 3–7 wt./wt. % aqueous solution, hydrogen peroxide is considered non-corrosive but an eye irritant; and at concentrations of above about 8 wt./wt. % aqueous solution, hydrogen peroxide is considered corrosive, more so at higher concentrations, and also a strong oxidizing agent.

The higher concentration levels of hydrogen peroxide solutions required to provide fast, effective action are not practical or economically viable, and may be subject to hazardous goods regulations and require special precautions for handling and use. Heretofore, one of the major drawbacks of hydrogen peroxide, in low concentrations, is that its antimicrobial action is too slow. A second major drawback is that it has not been considered possible to stabilize the peroxide sufficiently to make the solution commercially acceptable. For example, prior references indicate that a 0.1 wt./wt. % aqueous solution of hydrogen peroxide requires 60 minutes to disinfect surfaces contaminated with *staphylococcus aureus*, whereas a 25.8 wt./wt. % aqueous solution of hydrogen peroxide requires only 20 seconds to disinfect surfaces contaminated with *staphylococcus aureus*. The latter solution is clearly unacceptable for commercial use, both from a safety standpoint and an economic standpoint.

It has now been found that addition of phosphorus-based acids and anionic surfactants greatly enhance the activity of aqueous hydrogen peroxide solutions. The phosphorus-based acids are inorganic acids or organic acids. Especially preferred are phosphoric acid ($H_3PO_4$) and phosphonates having 1 to 5 phosphonic acid groups. Particularly preferred phosphonates are amino tri(methylene phosphonic acid), 1-hydroxyethylidene-1,1,-diphosphonic acid, diethylenetriaminepenta-(methylene phosphonic acid), 2-hydroxyethylimino bis(methylene phosphonic acid), ethylene diamine tetra(methylene phosphonic acid). Each may be used alone but mixtures of phosphoric acid and at least one of the phosphonates are preferred. Some of these phosphonic acids are available from Albright & Wilson under the trade mark BRIQUEST and some from Solutia Inc. under the trade mark DEQUEST. The concentration of the phosphorus-based acids is from 0.05 to 8.0 wt./wt. % of the solution. The lower concentrations are preferable for solutions with lower concentrations of hydrogen peroxide. The pH of the solutions are preferably from about 1 to about 9, particularly from 1 to 7, and even more particularly from about 1 to about 3.

The anionic surfactant is selected from the group consisting of C8 to C16-alkyl aryl sulphonic acids and alkali metal and ammonium salts thereof, sulphonated C12 to C22 carboxylic acids and alkali metal and ammonium salts thereof, C8 to C22-alkyl diphenyl oxide sulphonic acids and alkali metal and ammonium salts thereof, naphthalene sulphonic acids and alkali metal and ammonium salts thereof, C8 to C22 alkyl sulphonic acids and alkali metal and ammonium salts thereof, alkali metal C8 to C18 alkyl sulphates, and mixtures thereof, in a concentration range of from 0.02 to 5 wt./wt. % of the solution. Preferably, the anionic surfactant is an alkyl aryl sulphonate, especially a C10 to C16 alkyl benzene sulphonate or mixtures thereof. Preferred anionic surfactants are dodecyl benzene sulphonate, and tridecyl benzene sulphonate and their salts, e.g. sodium, potassium, ammonium salts. The alkyl aryl sulphonates are preferred because of their biodegradability.

Of the sulphonated C12 to C22 carboxylic acids, sulphonated 9-octadecanoic acid is preferred. Of the C8 to C22-alkyl diphenyl oxide sulphonic acids and salts, dodecyl diphenyl oxide disulphonic acid and disodium 4-dodecylated diphenyloxide sulphonate, alkylated sulphonated diphenyl oxide disodium salt are preferred. Of the C8 to C22 alkyl sulphonic acids, the sodium salts of 1-octane sulphonic acid, 1-decane sulphonic acid and tridecane sulphonic acid are preferred. Of the alkali metal C8 to C18 alkyl sulphates, sodium lauryl sulphate is preferred.

The hydrogen peroxide solution may be prepared as a concentrated aqueous solution, e.g. from up to 20 wt./wt. % hydrogen peroxide, preferably from up to 8 wt./wt. %, which then may be diluted by the end user, or the solution may be prepared in a dilute form, e.g. from 0.05 to 1.0 wt./wt. %. As will be illustrated by the examples which follow, solutions of about 0.5 wt./wt. % are effective in substantially reducing bacterial and viral activity.

Solutions having about from up to 0.05 to 1.0 wt./wt. % especially about 0.5 wt./wt. % hydrogen peroxide are suitable for use as household and commercial disinfectants, bactericides, virucides, sanitizers and cleaners. Solutions having about 3–4 wt./wt. % are suitable for use as multi-purpose cleaners and bleach alternatives in healthcare facilities, households and commercial facilities. Solutions having about 6–8 wt./wt. % hydrogen peroxide are suitable for use as a sporicides, fungicides, virucides, bactericides, broad spectrum sanitizers, general purpose cleaners and bleach alternatives, particularly in institutional, healthcare and food applications.

Other surfactants may be present as emulsifiers in the solutions. For example, certain emulsifiers are beneficial for cleaning surfaces with organic matter or grease and for providing stability to the solution. Typically, the emulsifiers are present in a concentration of about 10 to 30 parts emulsifier per hundred parts of hydrogen peroxide. Hydrotropes are preferred, particularly C8 to C16 alkylphenol alkoxylates.

Preferably, the emulsifiers are a mixture of polyoxyethylene and phenolethylene oxide emulsifiers in a concentration of about 0.1 to 0.2 wt./wt. % of the solution. The preferred emulsifiers are C8 to C16 alkylphenol alkoxylates, e.g. octyl phenol ethoxylate.

A short-chain alcohol, e.g. a C1–C6 alcohol, especially methanol, ethanol or iso-propanol, may be added to provide additional cleaning ability for organic contaminants. Preferred concentrations of the short chain alcohol are from about 0.1 to about 10 wt./wt. % of the composition. Addition of the alcohol is believed to provide better germicidal activity.

Because hydrogen peroxide has a broad spectrum of activity, it is useful in many different applications. In the healthcare field, the solution may be used in hospitals, clinics, laboratories, dental offices, home care and chronic care facilities. It may also be used in food and beverage processing and preparation, animal husbandry, the hospitality industry and for general sanitation, e.g. janitorial services.

The solutions of the present invention have a long shelf life, e.g. up to a year or more. This is surprising in view of the fact that previously known low concentration hydrogen peroxide solutions, e.g. about 0.5 wt./wt. % hydrogen peroxide solutions, generally break down quickly.

A preferred method for preparing the solutions of the present invention comprises adding the phosphorus-based acid(s) and the anionic surfactant(s) and optionally the emulsifiers to distilled or otherwise purified water prior to the addition of hydrogen peroxide. If there are any other ingredients, e.g. alcohols, scents, colouring agents, dyes, corrosion inhibitors these are preferably added before the hydrogen peroxide.

The invention may also be better understood by reference to the following examples:

EXAMPLE I

A solution of the present invention (Solution A) was prepared with 695 parts by weight distilled water, 20 parts by weight 75% phosphoric acid ($H_3PO_4$), 75 parts by weight 50% BRIQUEST 301-50A (trade mark) amino tri (methylene phosphonic acid), 25 parts by weight 45% hydrotrope DOWFAX (trade mark) alkylated sulphonated diphenyl oxide disodium salt emulsifier, 25 parts by weight 98% BIOSOFT (trade mark) dodecyl benzene sulphonic acid, 10 parts by weight TRITON X-405 70% (trade mark) octyl phenol ethoxylate emulsifier and 150 parts by weight 50% hydrogen peroxide. The ingredients were mixed in a passivated vessel, with hydrogen peroxide being the last ingredient added to the solution. The pH of the solution was 1.27.

Aliquots of this solution were tested for mycobacterial, sporicidal, fungicidal, bactericidal and virucidal activity and compared against commercially available disinfectants. For testing for bactericidal and virucidal activity, aliquots were diluted with water, with 1 part solution to 15 parts water.

Quantitative carrier tests were conducted on the samples. The test methods incorporated the essential requirements of the Canadian General Standards Boards' standard entitled "Assessment of Efficacy of Antimicrobial Agents for Use on Environmental Surfaces and Medical Devices" (CGSB 1997), and also conform to the ASTM requirements for evaluating virucidal activity of liquid germicides to be used on non-porous surfaces.

The inside bottom surface of glass vials was used as the carrier surface for mycobacterial, sporicidal, fungicidal, bactericidal tests. Stainless steel disks were used as the carrier surface for virucidal tests. Silk suture loops were not used because of the extreme difficulty in using them for standardized tests.

All test organisms were first suspended in bovine serum at a final concentration of 5%. When the product was to be tested after dilution, water with a standard hardness of 200 ppm as calcium carbonate was used as the diluent. The water was prepared according to the formula in AOAC International (1990).

Phosphate buffer, at pH 7.2 was used to make dilutions of spores and vegetative bacterial cells and to rinse membrane filters in tests for sporicidal and bactericidal tests. The diluent and filter rinse used for mycobactericidal and fungicidal tests was sterile normal saline (0.85% sodium chloride). Earle's balance salt solution was used to prepare dilutions of the virus prior to infectivity assays.

The general steps for quantitative analysis of mycobacterial, sporicidal, fungicidal and bactericidal activities of the test disinfectant involved i) inoculating carriers with inserts centred in vials, ii) dyeing the inoculated carriers, iii) removing the inserts, iv) adding a test disinfectant to the inoculated carrier, v) diluting of the test disinfectant at the completion of a known exposure time at a known temperature, vi) filtering and vii) placing the filters onto a medium, followed by incubating. The colony forming units (CFU) were then determined.

Control carriers were used in the same manner as test carriers, except that phosphate buffer was applied to the dried inoculum instead of disinfectant in the case of sporicidal and bacterial tests, and sterile saline was applied in the case of mycobactericidal and fungicidal tests. In the tests, there were three control carriers to every seven test carriers.

For virucidal activity, each stainless steel disk received test virus in bovine serum. After the inoculum had dried, it was exposed either to Earle's buffer solution or the test disinfectant for the required contact time and temperature. Each disk was placed in a vial with eluent/diluent and vortexed to recover the inoculum. The control and test eluates were inoculated into cell cultures for virus plaque assays. The plaque forming units (PFU) were then determined. To avoid false positive results, further controls were carried out by exposing the cell monolayers to a non-virucidal and non-cytotoxic dilution of the test products and then using the same monolayers for plaque assays. If the number of plaques on such pre-exposed monolayers was the same as those exposed to Earle's solution, the product was regarded as free from interference. In the tests, there were three control carriers to every five test carriers.

The test results are shown in Tables I and II.

TABLE I

| | | CFU** | |
|---|---|---|---|
| Organism | Contact time | Control | Solution A |
| ATCC 19659* | 6 hours | $1.96 \times 10^8$ | 0 |
| ATCC 7955* | 6 hours | $3.12 \times 10^7$ | 0 |
| ATCC 15442* | 10 minutes | $1.79 \times 10^6$ | 0 |
| ATCC 15442* | 3 minutes | $1.25 \times 10^6$ | 0 |
| ATCC 15442* | 1 minute | $1.45 \times 10^6$ | 0 |
| ATCC 6538* | 1 minute | $1.40 \times 10^6$ | 0 |
| ATCC 10708* | 1 minute | $1.16 \times 10^6$ | 0 |
| ATCC 15755* | 20 minutes | $1.86 \times 10^6$ | 0 |
| ATCC 9533* | 5 minutes | $4.0 \times 10^5$ | 0 |

TABLE II

| | | PFU** | |
|---|---|---|---|
| Organism | Contact time | Control | Solution A |
| ATCC VR-192* | 5 minutes | $8.7 \times 10^4$ | 1 |
| ATCC VR-192* | 5 minutes | $8.7 \times 10^4$ | 10 |

*ATCC 19659 *Bacillus subtilis*; *ATCC 7955 *Clostridium sporogenes*; *ATCC 15442 *Pseudomonas aeruginosa*; *ATCC 6538 *Staphylocccccus aureus*; *ATCC 10708 *Salmonella chloreræsuis*; *ATCC 15755 *Mycobacterium terrae*; *ATCC 9533 *Trichophyton mentagrophytes*; *ATCC VR-192* Sabin vaccine strain of polio virus Type I
**CFU = colony forming units; PFU = plaque forming units

EXAMPLE II

Solution A of Example I was tested further, according to the method of Germicidal and Detergent Sanitizing Action of Disinfectants, Final Action AOAC XV, 1995, Part 6.3.03.

Samples of the organism being tested were mixed with 5% bovine serum. 56 mL portions of Solution A were diluted with 4 litres of 200 ppm synthetic hard water. Each dilute solution was applied to an organism at 20° C. and the organism count per millilitre was determined before application of the solution, and 30 seconds and 60 seconds after application of the solution. The results are shown in Table III.

TABLE III

| Organism | Initial Count | Count 30 sec | Count 60 sec |
| --- | --- | --- | --- |
| ATCC 15442 | $94.5 \times 10^6$ | <10 | <10 |
| ATCC 6538 | $44.5 \times 10^6$ | 218 | 75 |
| ATCC 33592* | $32.3 \times 10^6$ | <10 | <10 |
| ATCC 51575* | $94.5 \times 10^6$ | <10 | <10 |

*ATCC 33592 *Staphylococcus aureus* (methicillin resistant); ATCC 51575 *Enterococcus fæcalis* (vancomycin resistant)

EXAMPLE III

Solution A of Example I was tested further, according to the method of Germicidal and Detergent Sanitizing Action of Disinfectants, Final Action AOAC XV, 1995, Part 6.3.03.

Samples of the organism being tested were mixed with 5% bovine serum. The undiluted Solution A was applied to the organisms at 20° C. and the organism count per millilitre was determined before application of the solution, and 30 seconds and 60 seconds after application of the solution. The results are shown in Table IV.

TABLE IV

| Organism | Initial Count | Count 30 sec | Count 60 sec |
| --- | --- | --- | --- |
| ATCC 10708 | $117 \times 10^6$ | <10 | <10 |
| ATCC 15442 | $94.5 \times 10^6$ | <10 | <10 |
| ATCC 6538 | $44.5 \times 10^6$ | <10 | <10 |
| ATCC 33592 | $79.5 \times 10^6$ | <10 | <10 |
| ATCC 51575 | $32.3 \times 10^6$ | <10 | <10 |

EXAMPLE IV

The test according to Example II was modified, using 50% bovine serum which was added to the organism. 56 mL portions of Solution A were diluted with 4 litres of 200 ppm synthetic hard water. Each dilute solution was applied to an organism at 20° C. and the organism count per millilitre was determined before and application of the solution, and 30 seconds and 60 seconds after application of the solution. The results are shown in Table V.

TABLE V

| Organism | Initial Count | Count 30 sec | Count 60 sec |
| --- | --- | --- | --- |
| ATCC 15442 | $235 \times 10^6$ | <10 | <10 |
| ATCC 6358 | $115 \times 10^6$ | <10 | <10 |
| ATCC 10708 | $81.3 \times 10^6$ | <10 | <10 |

EXAMPLE V

Tests were carried out to determine the cleaning efficiency of diluted solutions of Solution A compared to commercially available cleaners. Test Procedure CAN/CGSB 2.1, Method 20.3 was used, in which synthetic soil, of brown iron oxide pigment, kerosene, Stoddard solvent, white petroleum jelly, lubricating oil and shortening, was applied to white vinyl tiles. As a control, a 1% CGSB standard detergent in 125 ppm hard water, was used.

One portion of Solution A was diluted in 125 ppm hard water to form Solution B, which contained about 0.06% hydrogen peroxide. Another portion of Solution A was diluted in 125 ppm hard water to form Solution C, which contained about 0.01% hydrogen peroxide. A sample of commercial sodium hypochlorite bleach was diluted 1:20 to form Solution D.

The contaminated tiles were cleaned with 50 mL of each solution being tested and cleaning efficiency values were based on reflectance measurements. The results are shown in Table VI.

TABLE VI

| Solution | Efficiency (%) |
| --- | --- |
| Solution B (0.06% $H_2O_2$) | 94.6 |
| Solution C (0.01% $H_2O_2$) | 93.7 |
| Solution D (Na hypochlorite) | 11.3 |
| Standard Detergent | 77.2 |
| Distilled water | 11.4 |

What is claimed is:

1. An aqueous solution having a pH from about 1 to about 3 and consisting essentially of i) hydrogen peroxide in a concentration of from 0.05 to about 8.0 wt./wt. % of the solution, ii) at least one phosphorus-based acid selected from the group consisting of phosphoric acid and a mixture of phosphoric acid and phosphonates having 1 to 5 phosphonic acid groups, in a concentration range of from 0.05 to 8.0 wt./wt. % of the solution, and iii) at least one anionic surfactant selected from the group consisting of C8 to C16-alkyl aryl sulfonic acids and alkali metal and ammonium salts thereof, in a concentration range of from 0.02 to 5 wt./wt. % of the solution.

2. A solution according to claim 1 wherein the at least one anionic surfactant is dodecyl benzene sulfonic acid or an alkali metal or ammonium salt thereof.

3. A solution according to claim 1 wherein the solution has a hydrogen peroxide concentration of from 0.05 to 1.0 wt./wt. % of the solution.

4. An aqueous solution having a pH from about 1 to about 3 and consisting essentially of i) hydrogen peroxide in a concentration of from 0.05 to about 8.0 wt./wt. % of the solution, ii) at least one phosphorus-based acid selected from the group consisting of phosphoric acid and a mixture of phosphoric acid and phosphonates having 1 to 5 phosphonic acid groups, in a concentration range of from 0.05 to 8.0 wt./wt. % of the solution, iii) at least one anionic surfactant selected from the group consisting of C8 to C16-alkyl aryl sulfonic acids and alkali metal and ammonium salts thereof, in a concentration range of from 0.02 to 5 wt./wt. % of the solution, and (iv) up to about 3 wt./wt. % of at least one emulsifier.

5. A solution according to claim 4 wherein the emulsifier is selected from the group consisting of polyoxyethylene surfactants and hydrotropes.

6. A solution according to claim 5 wherein the hydrotrope is selected from the group consisting of an alkylated sulphonated diphenyl oxide and an alkylated sulphonated diphenyl oxide salt.

7. A solution according to claim 4 wherein the emulsifier is a C8 to C16 alkyl phenoxypolyethoxy ethanol.

8. A solution according to claim 5, containing phosphoric acid, a phosphonate having from 1 to 5 phosphonic acids groups, an alkylphenol alkoxylate, and an alkyated sulfonated diphenyl oxide salt.

9. An aqueous solution having a pH from about 1 to about 3 and consisting essentially of i) hydrogen peroxide in a concentration of from 0.05 to about 8.0 wt./wt. % of the solution, ii) at least one phosphorus-based acid selected from the group consisting of phosphoric acid and a mixture of phosphoric acid and phosphonates having 1 to 5 phosphonic acid groups, in a concentration range of from 0.05 to 8.0 wt./wt. % of the solution, iii) at least one anionic surfactant selected from the group consisting of C8 to C16-alkyl aryl sulfonic acids and alkali metal and ammonium salts thereof, in a concentration range of from 0.02 to 5 wt./wt. % of the solution, and (iv) from 0.1 to 10 wt./wt. % of an alcohol comprising one to six carbon atoms.

10. An aqueous solution having a pH from about 1 to about 3 and consisting essentially of i) hydrogen peroxide in a concentration of from 0.05 to about 8.0 wt./wt. % of the solution, ii) at least one phosphorus-based acid selected from the group consisting of phosphoric acid and a mixture of phosphoric acid and phosphonates having 1 to 5 phosphonic acid groups, in a concentration range of from 0.05 to 8.0 wt./wt. % of the solution, iii) at least one anionic surfactant selected from the group consisting of C8 to C16-alkyl aryl sulfonic acids and alkali metal and ammonium salts thereof, in a concentration range of from 0.02 to 5 wt./wt. % of the solution, and (iv) from 0.05 to 10.0 wt.wt % of a corrosion inhibitor.

11. An aqueous solution having a pH from about 1 to about 3 and consisting essentially of i) hydrogen peroxide in a concentration of from 0.05 to about 8.0 wt./wt. % of the solution, ii) at least one phosphorus-based acid selected from the group consisting of phosphoric acid and a mixture of phosphoric acid and phosphonates having 1 to 5 phosphonic acid groups, in a concentration range of from 0.05 to 8.0 wt./wt. % of the solution, iii) at least one anionic surfactant selected from the group consisting of C8 to C16-alkyl aryl sulfonic acids and alkali metal and ammonium salts thereof, in a concentration range of from 0.02 to 5 wt./wt. % of the solution, and (iv) a non-ionic surfactant selected from the group consisting of alkylated alkoxylate surfactants, alkyl aryl alkoxylate surfactants and mixtures thereof.

12. An aqueous solution having a pH from about 1 to about 3 and consisting essentially of i) hydrogen peroxide in a concentration of from 0.05 to about 8.0 wt./wt. % of the solution, ii) at least one phosphorus-based acid selected from the group consisting of phosphoric acid and a mixture of phosphoric acid and phosphonates having 1 to 5 phosphonic acid groups, in a concentration range of from 0.05 to 8.0 wt./wt. % of the solution, iii) at least one anionic surfactant selected from the group consisting of C8 to C16-alkyl aryl sulfonic acids and alkali metal and ammonium salts thereof, in a concentration range of from 0.02 to 5 wt./wt. % of the solution, and (iv) a monocarboxylic acid, a polycarboxylic acid, or mixtures thereof, in a concentration of from about 0.05 to about 4.0 wt./wt. % of the solution.

13. An aqueous solution having a pH from about 1 to about 3 and consisting essentially of i) hydrogen peroxide in a concentration of from 0.05 to about 8.0 wt./wt. % of the solution, ii) at least one phosphorus-based acid selected from the group consisting of phosphoric acid and a mixture of phosphoric acid and phosphonates having 1 to 5 phosphonic acid groups, in a concentration range of from 0.05 to 8.0 wt./wt. % of the solution, iii) at least one anionic surfactant selected from the group consisting of C8 to C16-alkyl aryl sulfonic acids and alkali metal and ammonium salts thereof, in a concentration range of from 0.02 to 5 wt./wt. % of the solution, and (iv) a hydrotrope selected from the group consisting of an alkylated sulfonated diphenyl oxide and an alkylated sulphonated diphenyl oxide salt.

14. A solution according to claim 13 wherein the hydrotrope is a C6 alkylated sulfonated diphenyl oxide salt.

* * * * *